United States Patent [19]
Yessik

[11] Patent Number: 4,862,888
[45] Date of Patent: Sep. 5, 1989

[54] LASER SYSTEM

[75] Inventor: Michael Yessik, San Francisco, Calif.

[73] Assignee: Bausch & Lomb Incorporated, Rochester, N.Y.

[21] Appl. No.: 244,523

[22] Filed: Sep. 9, 1988

Related U.S. Application Data

[63] Continuation of Ser. No. 104,562, Oct. 5, 1987, abandoned, which is a continuation of Ser. No. 939,269, Dec. 11, 1986, abandoned, which is a continuation of Ser. No. 546,740, Oct. 28, 1983, abandoned.

[51] Int. Cl.⁴ ............................................ A61B 17/36
[52] U.S. Cl. ............................. 128/303.1; 128/395; 219/121.61; 372/10; 372/25; 372/72; 372/103
[58] Field of Search ................... 128/303.1, 395–398; 372/10, 25, 69, 70, 72, 101, 103; 219/121 LA, 121 LB, 121.61, 121.62

[56] References Cited

U.S. PATENT DOCUMENTS

| | | | |
|---|---|---|---|
| 3,319,182 | 5/1967 | Aagard | 372/70 |
| 3,448,403 | 6/1969 | Vislocky | 372/72 |
| 3,500,231 | 3/1970 | Tomiyasu et al. | 372/72 X |
| 3,673,504 | 6/1972 | Hilberg | 372/10 |
| 3,806,829 | 4/1974 | Duston et al. | 372/25 |
| 3,979,696 | 9/1969 | Buchman | 372/72 |
| 4,156,209 | 5/1979 | Herbst et al. | 372/72 X |
| 4,309,998 | 1/1982 | Aron | 128/303.1 |
| 4,409,979 | 10/1983 | Roussel et al. | 128/303.1 |

FOREIGN PATENT DOCUMENTS

| | | | |
|---|---|---|---|
| 1541165 | 8/1969 | Fed. Rep. of Germany | 128/395 |
| 0082584 | 5/1983 | Japan | 372/10 |
| 1081011 | 8/1967 | United Kingdom . | |
| 1312600 | 4/1973 | United Kingdom . | |
| 1500428 | 2/1978 | United Kingdom . | |
| 1509365 | 5/1978 | United Kingdom . | |
| 1554823 | 10/1979 | United Kingdom . | |
| 2089107A | 6/1982 | United Kingdom . | |

OTHER PUBLICATIONS

Carlough et al., "Laser Pumping Cavity", IBM Tech. Dis. Bull., vol. 6, No. 11, Apr. 1964.
Daw et al., "Cast Plastic . . . Cavities", Applied Optics, vol. 3, No. 8, Aug. 1964, pp. 984–985.
Gaponov et al., "Pump-Lamp Enclosure . . . Laser", Soviet J. Quantum Elec., vol. 5, No. 7, pp. 838–839, Jul. 1975.

*Primary Examiner*—Lee S. Cohen
*Attorney, Agent, or Firm*—Bernard D. Bogdon

[57] ABSTRACT

A laser system which is compact, requires no cooling means and can produce either substantially continuous output or narrow single pulses of high intensity or pulse bursts comprises a closed spherical pumping cavity having a diffuse reflecting surface and a laser rod and a flashlamp mounted in non-parallel relationship in the cavity. The system is especially useful in ophthalmology.

31 Claims, 7 Drawing Sheets

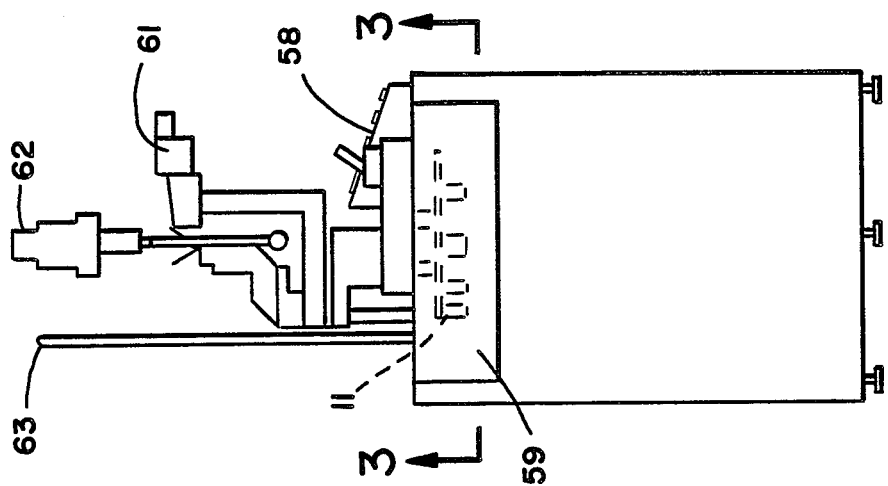
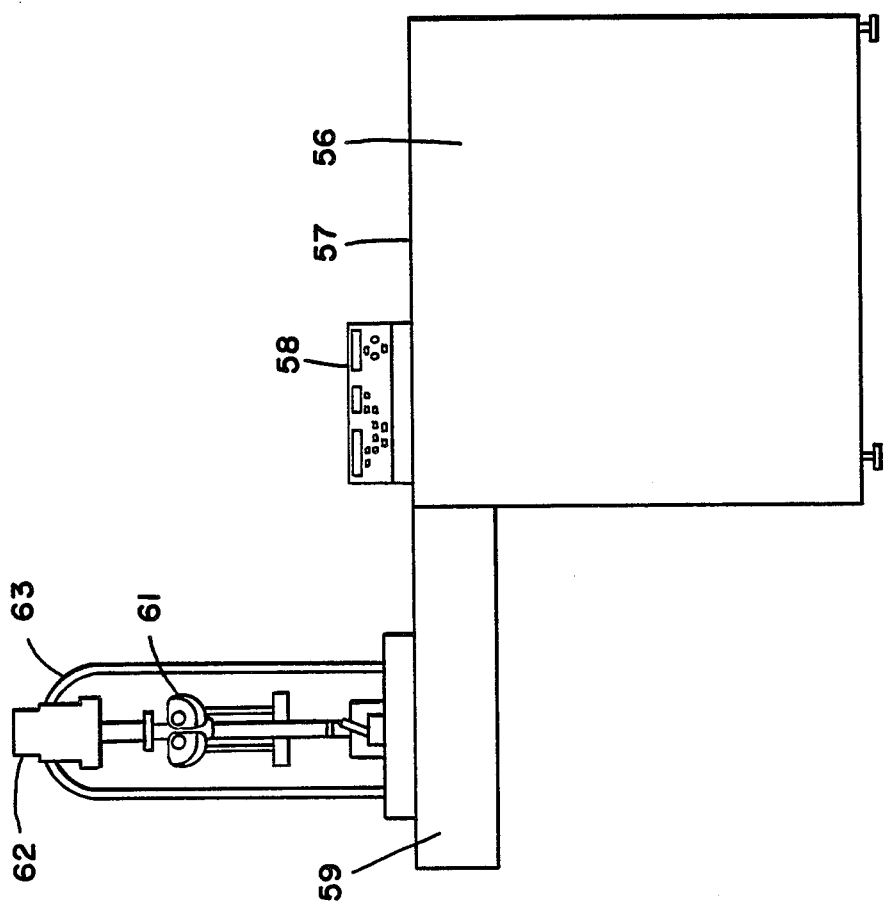

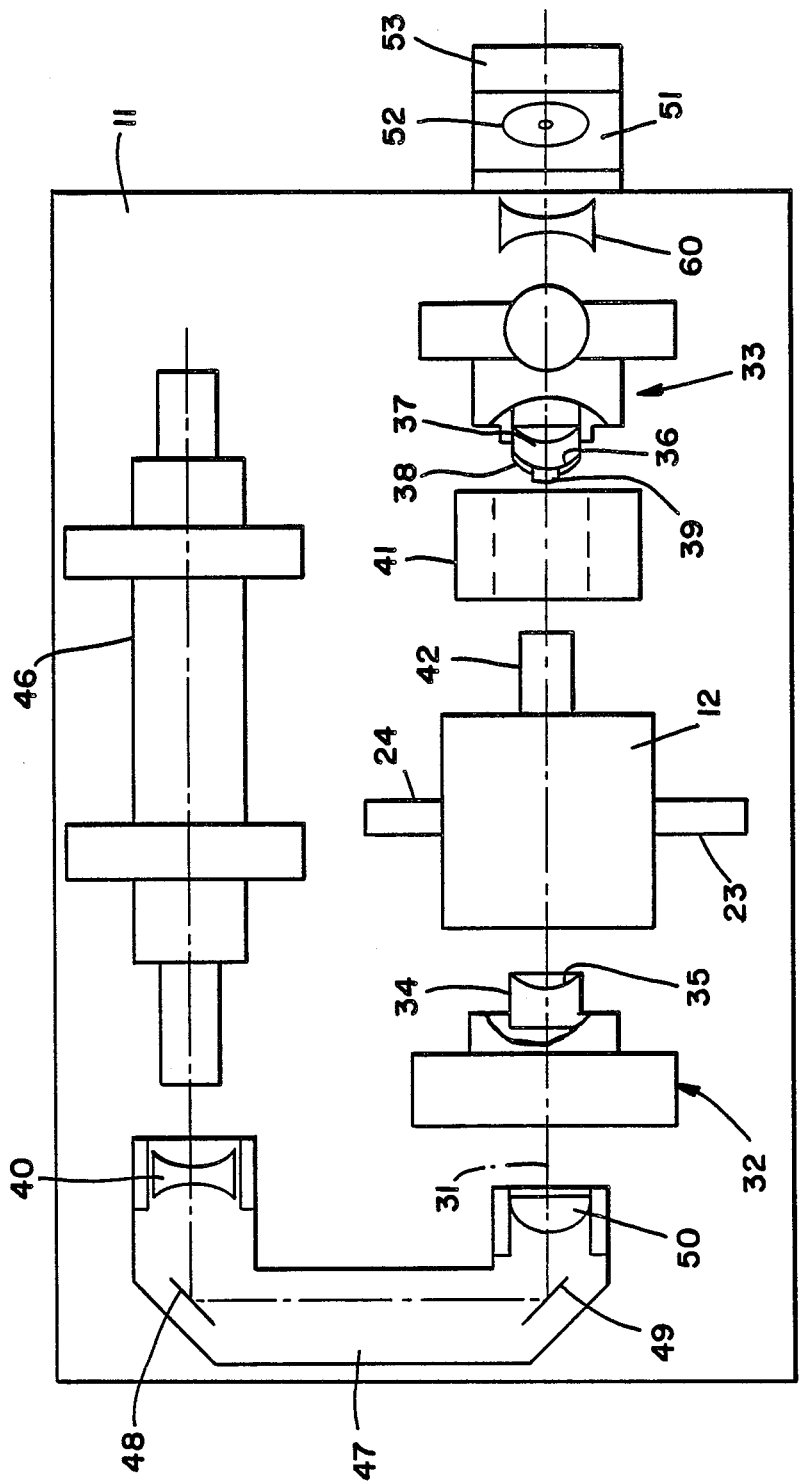
FIG_3

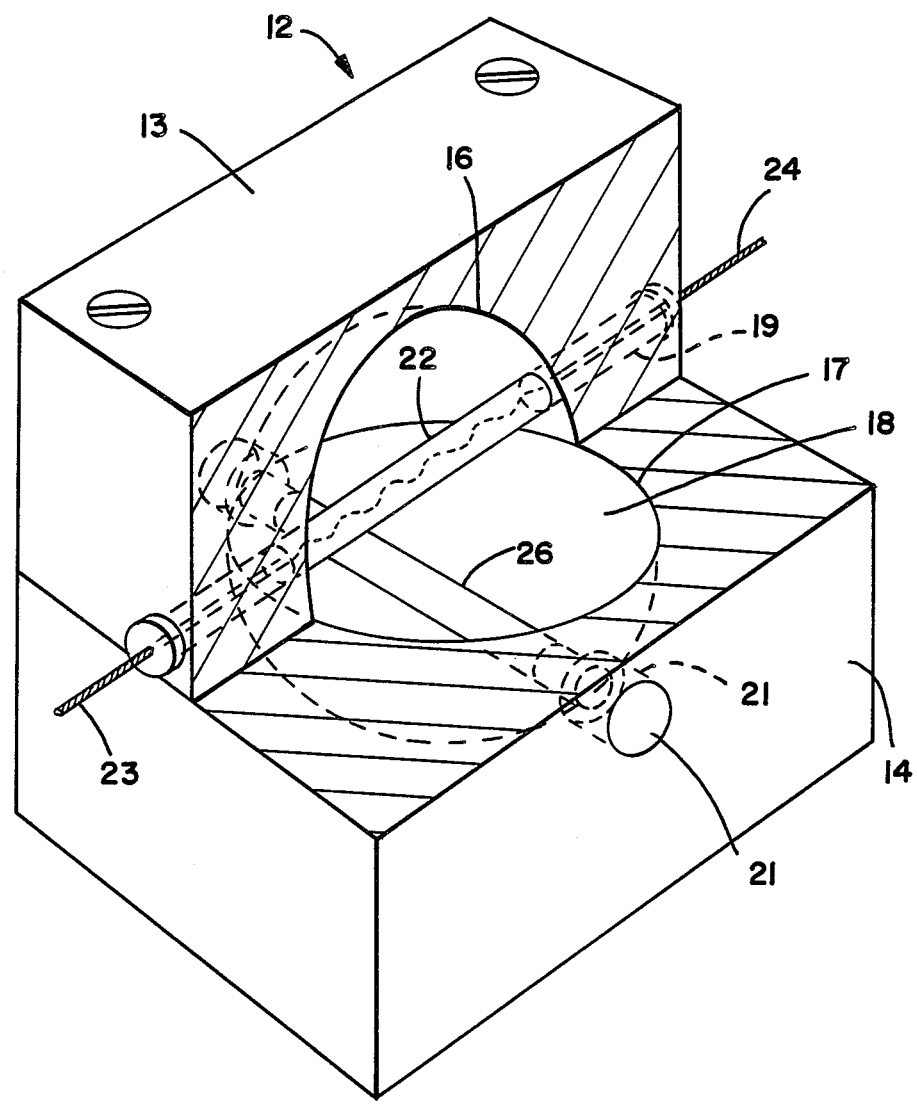
FIG_4

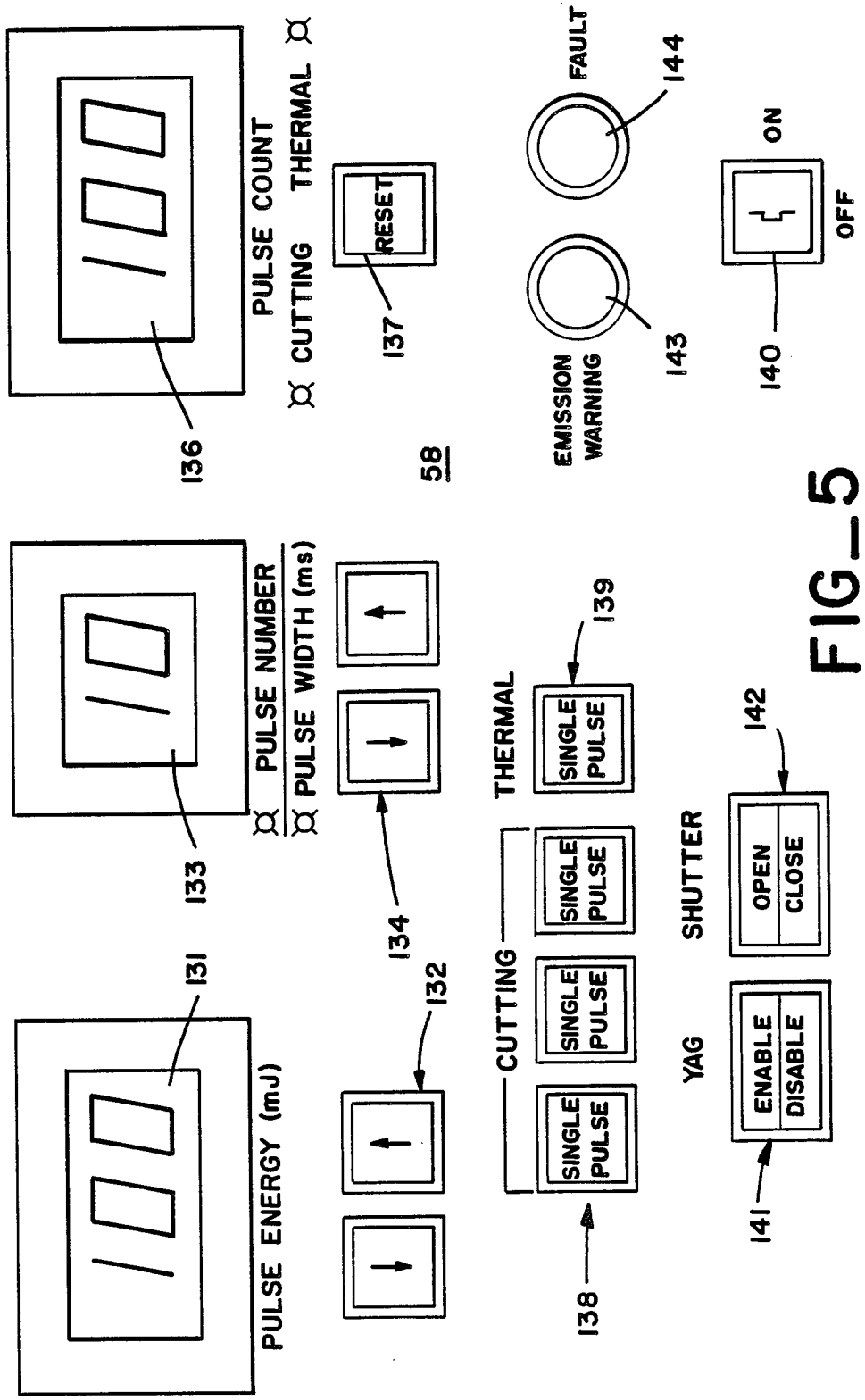
FIG_5

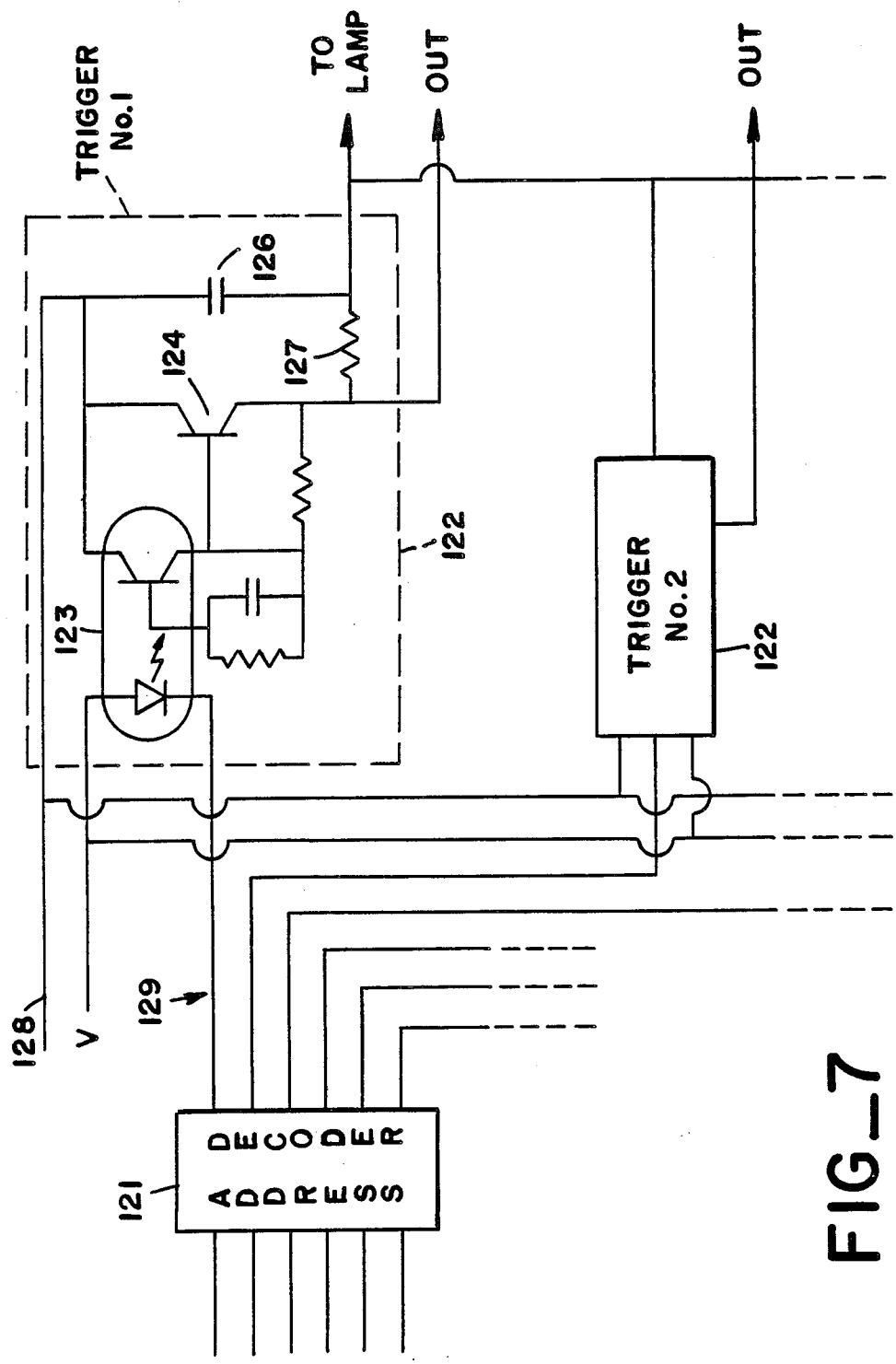
FIG_7

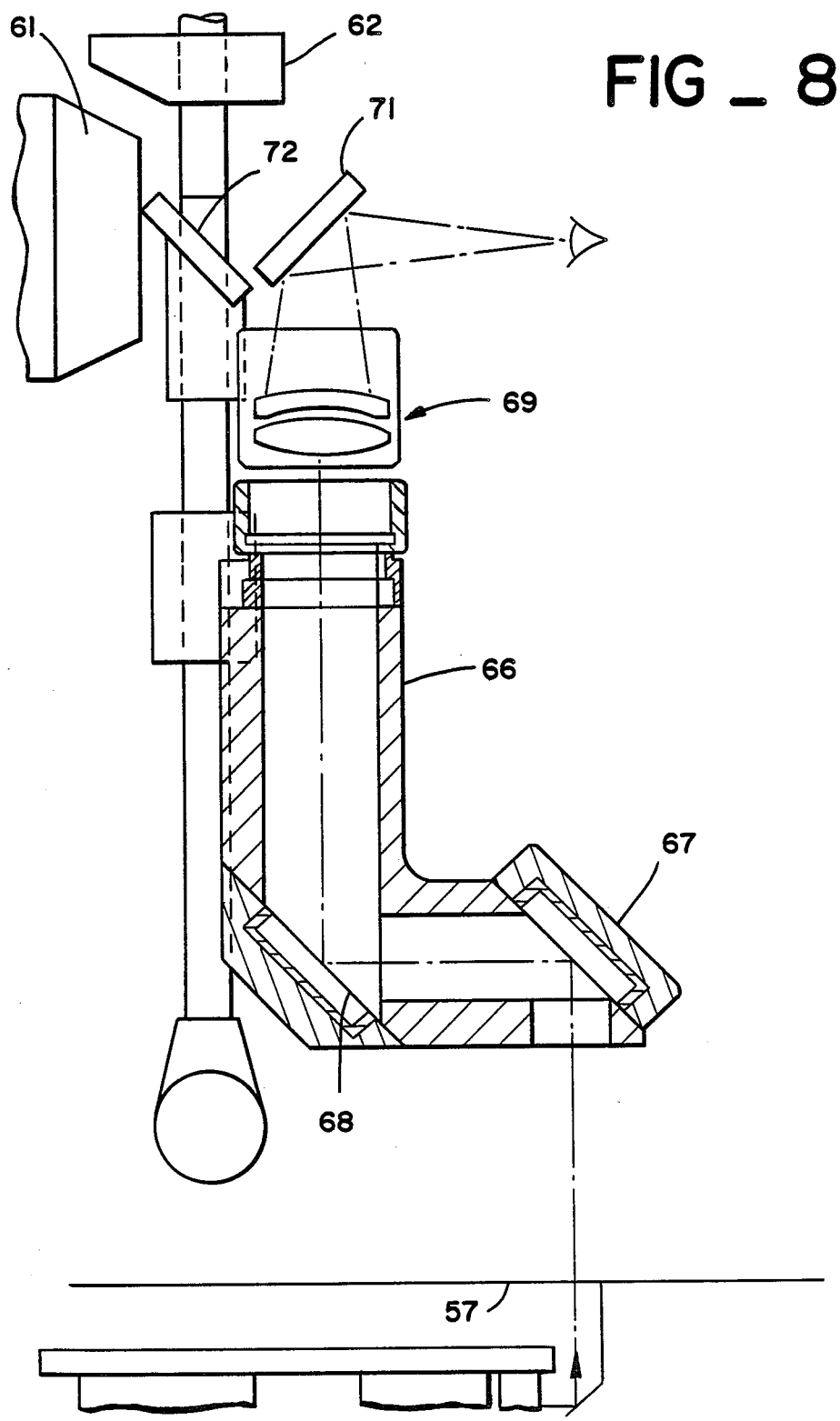
FIG_8

4,862,888

LASER SYSTEM

BACKGROUND OF THE INVENTION

This is a continuation of co-pending application Ser. No. 104,562 filed on Oct. 5, 1987, now abandoned, which is a continuation of application Ser. No. 939,269, filed on Dec. 11, 1986, now abandoned, which is a continuation of application Ser. No. 596,740, filed Oct. 28, 1983, now abandoned.

In recent years laser instruments have gained wide acceptance in the field of ophthalmological surgery, due primarily to the ability of laser systems to accomplish surgical tasks within the eye while causing little or no unwanted residual surgical trauma.

Surgical laser systems are used for such diverse purposes as photocoagulation of tissue to cutting and removal of tissue within the eye. In the former case, the procedure requires a relatively long laser illumination at a relatively low power intensity. In the latter case, it is necessary to use pulses of light energy of extremely short duration and high peak energy. Such pulses are capable of destroying the tissue at and around the focal point without causing undesirable thermal effects. It is generally true that systems capable of long-term laser illumination are not capable of generating the short, high intensity pulses required for some procedures.

A prior art system which exemplifies the state of the art of the latter case systems is disclosed in U.S. Pat. No. 4,309,998. This system is a Q-switched, mode-locked laser employing a YAG crystal to produce pulses of sufficient brevity and intensity to permit surgical cutting by optical puncture. Such a system, however, produces a series of closely spaced pulses in relatively uncontrolled fashion It is difficult to select precisely the desired output energy or number of pulses produced. Furthermore, this laser cannot be operated to produce the thermal effects which are necessary in some ophthalmological surgical procedures.

Also, the prior art system mentioned above is typical of the prior art in that it requires a cooling system to remove the heat generated in the relatively inefficient laser resonator. A cooling system is a mechanical system which requires maintainence, and which is subject to eventual failure. The cooling system also increases substantially the size of the laser system, making it more bulky and difficult to package in a usable and convenient form.

SUMMARY OF THE INVENTION

The present invention generally comprises a laser system adapted for ophthalmological use which is compact in configuration, simple to use and easy to maintain, and is capable of accomplishing surgical cutting by optical puncture as well as thermal effects such as photocoagulation and the like. The laser resonator of the present invention uses a novel optical pumping cavity to reduce the length of the resonator and thereby reduce the output pulse width. The novel cavity configuration also alleviates the need for a cooling system, thereby greatly simplifying the mechanical design of the system.

The optical pumping chamber includes a closed spherical cavity in which a Nd:YAG crystal and an excitation flashlamp are mounted in non-parallel fashion in the cavity. The small diameter, highly doped laser crystal is configured as an unstable resonator by a concave rear mirror and a convex front output mirror. A Q-switch is interposed between the crystal and one of the mirrors to permit selectively Q-switched and non-Q-switched operating modes. A continuous output gas laser is directed through the rear mirror and the laser crystal to provide a pilot beam for aiming and focussing. The laser outputs are directed to a focussing system through a slit lamp assembly, and both are directed into the eye of a patient to a common focus. The laser power supply includes a plurality of capacitors arrayed in banks and controlled by a microprocessor to deliver pulses of preselected voltage to the flashlamp singly or sequentially to produce single pulses, bursts of pulses, or repetitive pulses on command. A control system also operates the Q-switch in synchronism with the flashlamp, when Q-switching is desired. The system may be run in a thermal mode in which the laser crystal is stimulated by closely spaced repeated lamp flashes to cause the stimulated electron population inversion to be maintained. The resulting long train of pulses within a predetermined time-power envelope closely approximates a continuous output and produces the thermal physiological effects which are desirable for some laser surgical procedures. In the Q-switched mode, the combination of microprocessor control, a short optical pumping cavity, an unstable resonator configuration, and a small diameter, short length, high gain crystal produce very narrow pulses of high intensity, high beam quality, and precise duration, spacing, and energy.

BRIEF DESCRIPTION OF THE DRAWING

FIG. 1 is a front elevation of the laser system for ophthalmological surgery of the present invention.

FIG. 2 is a side elevation of the laser system depicted in FIG. 1.

FIG. 3 is a bottom view of the laser assembly of the present invention, taken along line 3—3 of FIG. 2.

FIG. 4 is a partially cutaway perspective view of the optical pumping chamber of the laser of the present invention.

FIG. 5 is a layout view of the control panel of the laser system of the present invention.

FIG. 7 is a functional block diagram of the control and supply circuits for the flashlamp firing system of the present invention.

FIG. 8 is a cross-sectional elevation of the optical output assembly of the laser system of the present invention.

DESCRIPTION OF THE PREFERRED EMBODIMENT

Figure 6:
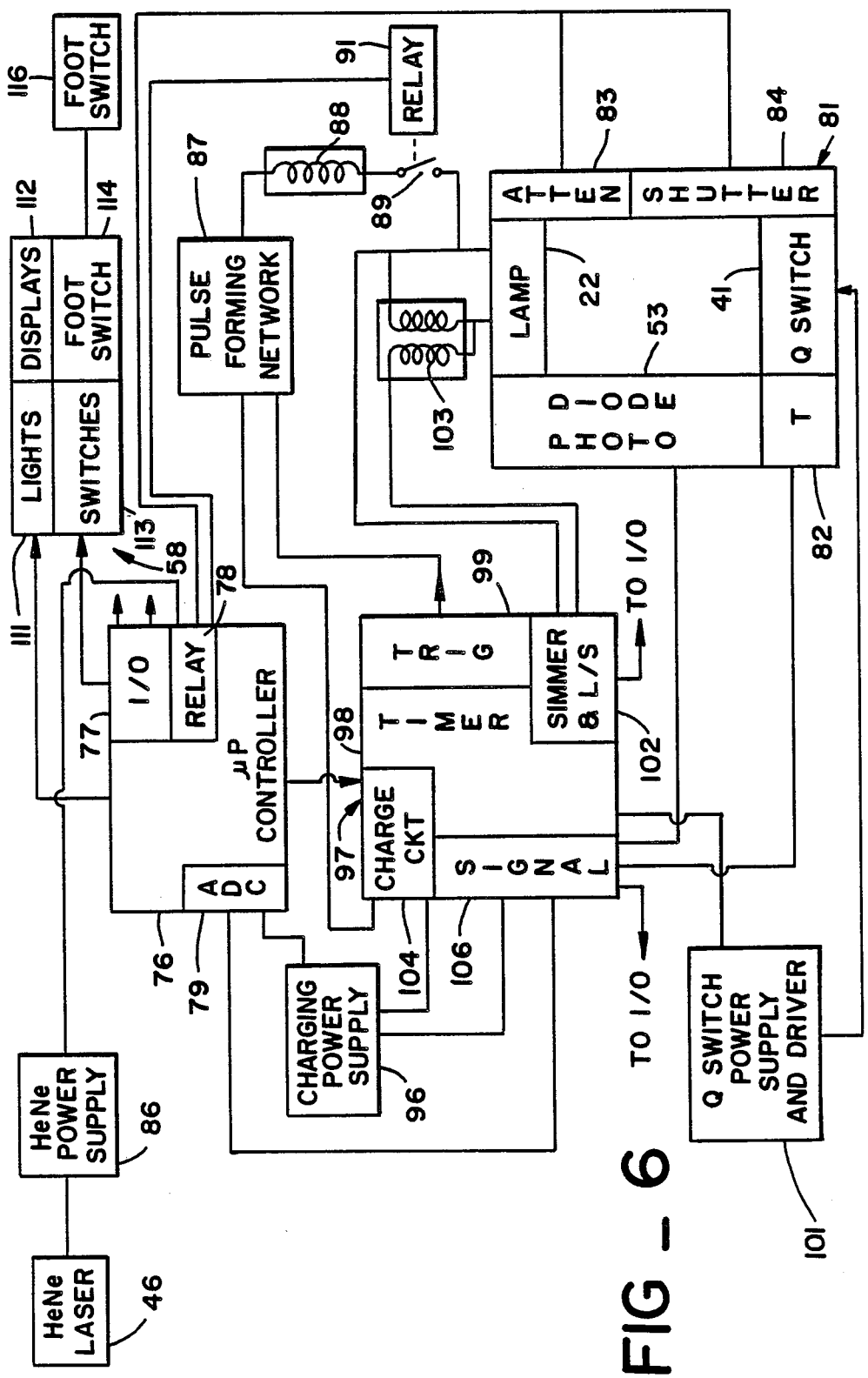
FIG. 6 is a functional block diagram of the control system of the laser system of the present invention.

The present invention generally comprises a laser system for ophthalmological surgical use which is compact in configuration, simple and easy to use and maintain, and capable of providing both tissue cutting and thermal effect outputs. The laser system also includes a microprocessor control system which provides precise selection of output pulse energy, pulse width, and number of pulses The laser can be operated in the Q-switch mode to generate single or multiple pulse trains, or it can be operated in a free-running "thermal" mode to mimic a continuous output and produce the thermal physiological effects of long term laser illumination.

With reference to FIG. 3, the laser configuration of the present invention includes a base plate 11 from which the operating components are suspended The base plate, which is approximately 6 inches by 10 inches, may be formed of Invar or similar material which exhibits a very low coefficient of thermal expansion. Secured to the base plate 11 is a novel optical pumping assembly 12, which is shown in greater detail in FIG. 4. The assembly includes a generally cubic body formed of a pair of rectangular solid members 13 and 14. Each of the members 13 and 14 includes a hemispherical cavity 16 and 17 formed in confronting faces thereof and disposed to be in exact registration when the members are joined together In the preferred embodiment, the cubic body is approximately 1.50 inches in side dimension, and the spherical cavity 18 formed by the two hemispherical cavities is approximately 1 inch in diameter The members 13 and 14 are formed of solid aluminum or material of similar thermal and structural properties, and are joined by screws received in tapped holes.

Each of the members 13 and 14 includes a bore 19 and 21, respectively, extending through the cavities 16 and 17. In the preferred embodiment the bores 19 and 21 are disposed in orthogonal fashion, although this arrangement is not critical for operation. The bores are disposed closely adjacent to the confronting faces of the members 13 and 14. Secured in the bore 19 is a flashlamp 22, with the output portion of the flashlamp disposed within the cavity 18 and the electrodes 23 and 24 protruding from the assembly 12. Secured in the bore 21 is a laser rod 26. In the preferred embodiment the laser rod is a Nd:YAG crystal which is highly doped with neodymium to provide a high amplification factor. The small diameter of the rod 26 enhances the efficiency of the system and the beam quality of the output.

The interior surface of the cavity 18 is treated with a highly efficient, diffusely reflective coating, the reflectivity being greater than 99%. A reflective material such as barium sulfate powder mixed with a binder may be applied directly to the interior surface of the cavity 18. For greater durability, the cavities 16 and 17 may be lined with glass hemispheres, and high purity barium sulfate powder without any binder may be secured between the outer surface of the hemispheres and the interior surfaces of the cavities.

The assembly 12 is secured to the base plate 11 with the bore 21 and laser rod 26 aligned precisely with the optical axis. The optical pumping assembly is disposed within a laser resonator defined by mirror assemblies 32 and 33. Mirror assembly 32 includes a 50 cm radius spherical radius of curvature mirror 34 with a concave surface 35 which is coated with multilayer dielectric materials to be greater than 99% reflective at the YAG laser wavelength of 1.064 micrometers. Mirror assembly 33 includes a convex surface 36 of 33 cm spherical radius of curvature. This mirror is formed on a meniscus substrate 37 with antireflective coatings 38 (at the YAG laser wavelength) applied to both surfaces of the substrate. At the center of the convex surface a coating which is highly reflective at the YAG laser wavelength is deposited over a 2.2 mm diameter spot to form a reflective spot 39.

It may be appreciated that the focus of the beam from the mirror 34 is proximate to the spot 39, so that a portion of the laser output is reflected back into the laser rod. The annular surround 38 of antireflective material serves as an output coupler for the laser beam which passes therethrough and on toward the beam utilization apparatus. In the unstable laser resonator defined by the mirror assemblies, all of the potential laser output is realized in the fundamental mode, so that all of the available laser energy is focussed into the smallest possible spot. Furthermore, the spot output coupler delivers a high proportion of the beam, reducing multiple reflections axially through the laser rod and permitting the generation of extremely short pulses.

The laser assembly also includes a Q-switch 41 interposed along the optical axis between the laser rod and one of the mirrors 34 and 39. In the preferred embodiment the Q-switch is disposed between the laser rod and the output mirror assembly 33, so that the laser rod is more fully illuminated by the wider portion of the laser beam reflecting between the mirrors. The Q-switch may comprise a transverse field electrooptic modulator using a lithium niobate crystal and a single, multilayer dielectric thin film polarizer 42, as is known in the prior art. In Q-switched operation the crystal is biased at a positive voltage to its quarter-wave retardation level to block laser action. Switching action is provided by a negative-going step pulse which is generated upon command by the control circuitry to shift the beam polarization and permit laser action. However, it is also quite possible to achieve non Q-switched laser operation without removing the Q-switch or the thin film polarizer.

Also secured to the baseplate 11 is a continuous output, visible light, low power laser 46, preferably a helium-neon (HeNe) gas laser. The output beam from the laser 46 is directed along the optical axis to a 180° reflector assembly 47. The assembly 47 includes a pair of mirrors 48 and 49 disposed at an angle of 45° to the incident beam from the laser 46. A diverging lens 40 and a converging lens 50 disposed at the entrance and exit, respectively, of the reflector assembly 47 form a collimator which equalizes the diameter of the HeNe beam to the diameter of the YAG beam. The HeNe beam exits from the lens 50 and is directed through the mirror 35, and through the laser rod, which are both substantially transparent to the HeNe wavelength, 633 nm. The output mirror 33 is also transparent to the HeNe beam, so that the two laser beams exit from the mirror assembly 33 in colinear alignment.

From the mirror assembly 33 the beams are directed through a beam spreading lens 60 to a mirror assembly 51 where a mirror 52 is used to reflect the beams 90° upwardly. The beam spreading effect permits a highly converging focus at the surgical site within the eye, so that only the tissue desired to be cut or treated is affected by the laser pulses. The spread beam also reduces the criticality of the subsequent mirror and lens surfaces and materials by reducing the energy density of the beam. Secured to the assembly 51 is a photosensor assembly 53, which receives approximately 1% of the beam energy transmitted through the mirror 52. The output of the photosensor is connected to the control system to provide a closed loop feedback system for recalibrating the energy output of the laser with respect to the light energy input, as will be explained in the following description.

With reference to FIG. 1 and 2, the invention also comprises a complete system for utilizing the laser describe above to perform ophthalmological surgery. The apparatus includes a cabinet 56 which is adapted to house the electronic power supplies and controls of the system. The cabinet includes a top surface 57 on which a control panel 58 is supported. A cantilever table 59 extends outwardly from one side of the cabinet The table 59 is supported by the cabinet in vertically translatable fashion to adjust to the height of the patient to be treated. The open end configuration of the table 59 permits access to and use of the instrument by individuals confined to a wheelchair. The feature is significant when it is considered that many patients requiring laser ophthalmological surgery are aged and frequently physically disabled. The baseplate of the laser assembly is secured to the table 59 in inverted fashion beneath the top thereof. Supported on the table 59 is a binocular examining microscope 61, a standard slit lamp assembly 62, and a frame 63 adapted to brace and restrain the head of the patient to be treated. It may be appreciated that the entire laser surgical system, requiring no ancillary equipment for operation and no cooling system, is fixedly secured to the slit lamp biomicroscope, and is translated vertically therewith. Thus misalignment problems are reduced, and moving mirrors, a source of failure in prior art systems, are eliminated entirely. Furthermore, the entire system occupies the space of a small desk.

With reference to FIG. 8, as the beams travel from the mirror 52 they pass through a hole in the top 57 and pass into a beam delivery assembly 66. The assembly 66 includes a pair of mirrors 67 and 68 aligned in generally parallel fashion to deliver the laser beams to a lens doublet 69 which focusses the beams. They are then reflected by reflecting mirror 71 to a focus inside the eye of the patient. The slit lamp projector is directed toward a mirror 72 which reflects that light source into the eye through the mirror 71. The surgeon's microscope 61 is directed through the mirror 71 and about the sides of mirror 72 to view the convergence of the beams within the eye, and the position and size of the focal spot. To enable the HeNe alignment beam to be conveniently focussed at the same point as the YAG pulses, the doublet is designed and fabricated to have the same focal length at 1064 nm and 633 nm. In the preferred embodiment, a selection of such achromatized lenses is made available to enable the focal spot diameter to be varied according to the requirements of the ophthalmological procedure.

Due to the fact that the laser assembly is secured directly to the slit lamp assembly, there is little opportunity for alignment problems to occur in the present system. This close proximity also reduces the number of mirrors used, especially compared to prior art articulated arm delivery systems, thereby further increasing overall reliability.

A salient feature of the present invention is the sophisticated control system which permits precise selection of the pulse energy, pulse width, and number of pulses delivered by the laser to the surgical site. The control system is depicted schematically in FIG. 6, wherein the large functional circuit blocks are subdivided into functional units where appropriate. Also, the many electrical power supplies for the circuits are not shown, for clarity and brevity.

With reference to FIG. 6, a significant feature of the control system is the provision of a microprocessor controller 76, complete with the necessary ROM, RAM, and programming to carry out the functions described in the following. The microprocessor controller also includes an input/output (I/O) section 77, a relay operating section 78, and an analog/digital (ADC) converter section 79. The control system also includes circuitry 81, comprising all of the electrical devices mounted on the laser assembly except the HeNe laser. This circuitry includes the flashlamp 22, the photodiode 53 which senses the energy of the YAG output beam, and the Q-switch 41. In addition, a thermistor 82 is secured to the laser body 12 to measure the temperature therein. The circuitry 81 also includes the solenoids to operate a laser beam attenuator 83 and a shutter 84, both being standard items in the prior art and neither being shown for the sake of clarity. The relay driver section 78 of the microprocessor controller is connected to both the attenuator 83 and the shutter 84. The relay section 78 is also connected to the HeNe power supply 86, which in turn energizes the HeNe laser 46.

The electrical system further includes a pulse forming network 87 which generates high voltage pulses of preselected voltage, spacing, and number The high voltage pulses are fed through an inductor 88 and through normally open relay contacts 89 to the flashlamp 22. The relay 91 which operates the contacts 89 is connected to the relay driver section of the microprocessor controller. The pulse forming network receives the high voltage required for the pulses from a charging power supply 96 through the charge circuit 104.

A flashlamp control circuit 97 is also provided to operate the flashlamp 22. The circuit 97 includes a timer section 98 which delays and controls the firing of the negative going pulse which operates the Q-switch driver and power supply 101. In Q-switched operation the Q-switch is opened approximately 70 microseconds after the flashlamp is fired by the high voltage pulse, to permit laser action to peak before the pulse is delivered. A trigger section 99, connected to the pulse forming network 87, is also provided to actuate the pulse forming network upon command from the microprocessor controller 76.

The flashlamp control circuit 97 further includes a section 102 (simmer- L/S) which starts the flashlamp and maintains an ionized state in the flashlamp thereafter by providing a "simmer" current of approximately 30 ma from a controlled current source. The lamp start procedure is accomplished by the section 102 delivering a sharp pulse to the pulse transformer 103. The pulse transformer generates a pulse of several kilovolts, sufficient to create a discharge through the flashlamp and begin operation. (The Q-switch and the shutter remain closed.) The simmer current is then sufficient to maintain the lamp in readiness to be flashed by the 200–400 volt pulses from the pulse forming network 87. It may be appreciated that the relay contacts 89 are maintained open during the lamp start procedure, so that the high voltage starting surge will not damage the pulse forming network. The circuit 97 also includes a signal conditioning section 106 which is connected to the thermistor 82 and the photodiode sensor 53. The section 106 conditions the signals from the thermistor and the photodiode, and delivers them to the analog/digital converter 79 of the microprocessor controller 76. The microprocessor controller integrates the photodiode signal to derive the beam energy of the YAG laser directly after it is fired. The thermistor signal is monitored reiteratively to assure that the temperature of the laser system is not exceeding the operating parameters stored in memory. Furthermore, the controller is programmed with a formula which determines the voltage from the charging power supply which must be applied to the flashlamp 22 to generate a laser pulse of desired energy. If the photodiode senses that the generated pulse differs significantly in beam energy from the desired setting, the microprocessor controller is programmed to alter the formula to agree more closely with measured output. Thus a closed feedback loop is constantly recalibrating the laser system output to be as precise and exact as possible.

The control system also includes the control panel 58 connected to the microprocessor controller which permits the surgeon to select the operating mode, pulse energy and spacing, and the like. The panel 58 includes indicator lights 111, LED or LCD displays 112, and numerical and functional setting switches 113. In addition, the control panel circuitry includes a foot switch operating circuit 114 connected to a foot switch 116 which permits control of the firing of the laser system by pedal rather than manual control of the surgeon.

With reference to FIG. 7, the pulse forming network trigger circuit, generally indicated at reference numeral 99, includes an address decoder 121 which receives from the microprocessor controller the numerical addresses of one or more of a plurality of pulse forming networks, and their respective trigger circuits 122. In the preferred embodiment there are 56 pulse forming networks (PFN), each having their own trigger circuit 122. Forty of the PFNs are connected in five arrays of eight each, primarily to ease interfacing with a binary digital microprocessor. Twelve of the PFNs are individually operable, and four are spares which can be substituted by the microprocessor controller for any PFN that may fail. Each trigger circuit is connected to its respective PFN in similarly arrayed fashion.

Each PFN trigger 122 includes an opto-isolator 123 which is connected to the base of transistor 124. A capacitor 126 is connected between the collector of transistor 124 and limiting resistor 127, which in turn is connected to the emitter. The capacitor is connected to a low voltage charging line 128. When a network 122 is selected by the microprocessor to provide a pulse to the flashlamp, all eight of the PFNs in that array are charged to a voltage determined by the microprocessor controller through the charging line 128. The address of the selected network is sent to the decoder 121, which grounds the signal line 129 of the appropriate PFN trigger The LED of the opto-isolator is caused to actuate, thereby switching on the transistor 124. When transistor 124 is caused to conduct, the charge on the capacitor is applied to the gate of the SCR of the respective PFN. Each PFN within the functional block 87 includes a large capacitor charged by the power supply 96 and connected through an SCR to the flashlamp. When the SCR is actuated, the resulting discharge produces a flashlamp pulse of approximately 50 microsecond duration, the intensity of the pulse being related in a predetermined, empirically derived manner to the voltage of the discharge. This known relationship permits the microprocessor controller to select the appropriate charging voltage to cause the requisite flash intensity to produce the desired laser pulse energy.

It may be appreciated that each flashlamp pulse will produce one laser output pulse. The microprocessor controller may fire the PFNs in single fashion, or in serial, spaced apart fashion to produce a pulse train of predetermined pulse energy, spacing, and pulse width. For each output pulse in the Q-switched mode, the Q-switch is opened approximately 70 microseconds after the lamp discharge commences. The laser system of the preferred embodiment is capable of delivering pulses of 5–10 nsec duration. These pulses can be delivered singly, or in bursts of 1–10 pulses in a 10 millisecond interval, or may be generated in repetitive fashion at a 3 Hz rate.

A significant feature of the operation of the present invention is that it is capable of operating in a free-running mode in which the output produces the thermal physiological effects which are required for photocoagulation and the like. In this "thermal" mode, the laser system can deliver a series of 100–500 mJ pulses of 50 microsecond duration in a period of 1–10 milliseconds. This operation is accomplished by charging the required PFNs to the necessary voltage, opening the Q-switch and the shutter, and firing the PFNs at 50–200 microsecond intervals. The first lamp discharge causes a significant population of the neodymium electrons to jump to the laser emission level, and a laser pulse is generated. However, the electron population inversion in the emission band persists briefly, for approximately 400 microseconds. The rapid flashlamp firing of the thermal mode takes advantage of this population inversion persistence by causing restimulation of the laser before the energy put into establishing the electron population inversion is lost. As a result, the present invention operates very efficiently in the free-running, "thermal" mode, and this mode is achieved without any cooling system. The overall envelope of the thermal mode pulses, considering their energy versus time characteristics, produces physiological effects identical to long term thermal pulses delivered by gas lasers and the like. Thus the present invention is capable of a flexibility in operating modes which has heretofor been unobtainable.

With reference to FIG. 5, the control panel 58 includes an LED readout 131 which displays the desired pulse energy setting of the YAG laser. Companion setting buttons 132 are provided to permit the surgeon to increment the setting upwardly or downwardly. An LED readout 133 displays both the pulse width setting and the number of pulses desired. Setting buttons are provided to select either display and to increment the settings. LED readout 136 displays the number of pulses delivered by the laser, and is resettable by button 137. A plurality of buttons 138 are provided to select the laser output in the cutting mode in which tissue is severed by optical puncture. These buttons may select either a single pulse, a continuous pulse train at a 3 Hz rate, or a burst of pulses. Selector button 139 permits the surgeon to select the thermal operating mode in which the laser provides a pulse train which produces the effect of a single, long term thermal pulse. Switches 141 and 142 enable the YAG laser and operate the shutter, respectively. Warning lights 143 and 144 indicate a problem with the laser emission and with the overall system, respectively Switch 140 is a key operated on-off switch.

I claim:

1. A multimode laser system comprising a laser rod secured in an optical pumping cavity defined by a closed, continuously curved surface, an excitation flashlamp for generating radiation disposed in said pumping cavity in a non-parallel and non-helical relationship with said laser rod, means for providing diffuse reflection of high reflectivity within the interior of said pumping cavity, mirror means axially disposed with respect to said laser rod for defining an unstable laser resonator with said laser rod, control means for actuating said flashlamp with electrical pulses of predetermined voltage, temporal spacing, and number in order to excite said laser rod and thereby to produce laser output pulses, and means for delivering said laser output pulses.

2. The multimode laser system of claim 1, further including Q-switch means for Q-switching said laser output pulses interposed between said mirror means and said laser rod, said control means including means for actuating said Q-switch means in timed synchronism with said flashlamp actuation.

3. The multimode laser system of claim 2, wherein said control means includes a microprocessor controller.

4. The multimode laser system of claim 3, further including Q-switch means for Q-switching said laser output pulses, and said microprocessor controller including program means for opening said Q-switch means, actuating said flashlamp with closely spaced pulses, and permitting said laser rod to lase in a free-running thermal mode.

5. The multimode laser system of claim 4, wherein said pulses are temporally spaced by an interval less than the decay time of the electron emission band population inversion of said laser rod to achieve high gain operation.

6. The multimode laser system of claim 3, further including Q-switch means for Q-switching said laser output pulses, and said microprocessor controller including program means for operating said Q-switch means in timed synchronism with said flashlamp actuation to achieve Q-switch mode operation.

7. The multimode laser system of claim 3, further including a plurality of pulse forming networks connected to said flashlamp and actuated in response to signals from said microprocessor controller.

8. The multimode laser system of claim 7, wherein said pulse forming networks are arrayed in binary addressable form.

9. The multimode laser system of claim 3, further including a photosensor disposed to receive a portion of said laser output pulses.

10. The multimode laser system of claim 9, wherein said microprocessor controller includes means for integrating the signal from said photosensor to determine the energy of said output pulses.

11. The multimode laser system of claim 10, further including feedback loop means in control means for altering said predetermined voltage applied to said flashlamp when the measured energy of said output pulses diverges from the expected pulse energy.

12. The multimode laser system of claim 1, wherein said surface comprises a sphere.

13. The multimode laser system of claim 1, wherein said laser rod and said flashlamp are disposed in closely spaced, substantially orthogonal relationship.

14. The multimode laser system of claim 1, wherein said pumping cavity is disposed in a laser body member, said member being formed of a material having high thermal conduction and capacity.

15. The multimode laser system of claim 1, wherein said means for providing diffuse reflection comprises a coating of barium sulfate powder and means for securing said powder to the interior surface of said pumping cavity.

16. The multimode laser system of claim 1, wherein said mirror means includes a first concave mirror and a second convex mirror disposed on either side of said laser rod.

17. The multimode laser system of claim 16, wherein said second mirror includes a centrally deposited spot having a coating highly reflective at the wavelength of said laser output pulses, and an annular surround about said spot formed of an anti-reflective coating to pass a portion of said laser output pulses and serve as an output coupler.

18. The multimode laser system of claim 17, further including a continuous output gas laser having an output beam directed along the optical axis of said laser rod in alignment with said laser output pulses.

19. The multimode laser system of claim 18, wherein said mirrors are substantially transparent to the wavelength of said output beam of said gas laser.

20. The multimode laser system of claim 1, wherein said laser rod is formed of Yttrium-Aluminum-Garnet, and is relatively highly doped with Neodymium to form a high gain laser rod.

21. An optical pumping assembly for a laser, including a laser body member, said member having a cavity therein defined by a closed and continuously curved surface, a laser rod extending through said cavity, the axis of said rod defining an optical axis, a flashlamp extending through said cavity in a non-parallel and non-helical relationship with the axis of said laser to minimize direct illumination of said laser rod, and a high efficiency diffusely reflective coating on said surface of said cavity to maximize diffused and uniform illumination of said laser rod from said surface of said cavity.

22. The optical pumping assembly of claim 21, wherein said cavity is spherical in configuration.

23. The optical pumping assembly of claim 21, wherein said flashlamp is disposed generally orthogonally with respect to said laser rod and spaced closely thereto.

24. The optical pumping assembly of claim 21, wherein said laser body member is formed of material of high thermal conductivity and capacity.

25. The optical pumping assembly of claim 21, wherein said flashlamp is linear in configuration.

26. The optical pumping assembly of claim 25, wherein said flashlamp is disposed generally orthogonally with respect to said laser rod and spaced closely thereto.

27. The optical pumping assembly of claim 21, wherein said member is formed of a material having high thermal conduction and thermal capacity.

28. A laser resonator comprising a laser body member, said member having a cavity therein defined by a closed and continuously curved surface, a laser rod extending through said cavity, the axis of said rod defining an optical axis, a flashlamp extending through said cavity in a non-parallel and non-helical relationship with the axis of said laser rod to minimize direct illumination of said laser rod, a high efficiency diffusely reflective coating on said surface of said cavity to maximize diffused illumination of said laser rod from said surface of said cavity, and mirror means axially disposed with respect to said laser rod for defining an unstable laser resonator with said laser rod.

29. The laser resonator of claim 28, wherein said mirror means includes a first concave mirror and a second convex mirror.

30. The laser resonator of claim 29, wherein said first and second mirrors includes a centrally disposed spot having a coating highly reflective at the laser wavelength, an annular surround about said spot formed of an anti-reflective coating to pass a portion of a beam produced by said laser rod and serve as an output coupler.

31. The laser resonator of claim 28, further including Q-switch means, for Q-switching an output of said laser rod, positioned between one of said first and second mirrors and said laser rod, and means for actuating said Q-switch means in timed synchronization with actuation of said flashlamp actuation.

* * * * *